(12) United States Patent
Chapaton et al.

(10) Patent No.: US 6,828,283 B2
(45) Date of Patent: Dec. 7, 2004

(54) TRACTION FLUID WITH ALKANE BRIDGED DIMER

(75) Inventors: Thomas J. Chapaton, Sterling Heights, MI (US); Tenneille W. Capehart, Rochester, MI (US); James L. Linden, Rochester Hills, MI (US)

(73) Assignee: Genberal Motors Corporation, Detroit, MI (US)

( * ) Notice: Subject to any disclaimer, the term of this patent is extended or adjusted under 35 U.S.C. 154(b) by 116 days.

(21) Appl. No.: 10/359,026

(22) Filed: Feb. 5, 2003

(65) Prior Publication Data

US 2004/0152931 A1 Aug. 5, 2004

(51) Int. Cl.[7] .................... C10M 105/02; C07C 13/18
(52) U.S. Cl. ................. 508/110; 585/20; 585/22
(58) Field of Search ............. 508/110; 585/20, 585/22

(56) References Cited

U.S. PATENT DOCUMENTS

| | | | | |
|---|---|---|---|---|
| 4,371,726 A | | 2/1983 | Horita et al. ............ 585/3 |
| 4,675,459 A | * | 6/1987 | Yuasa et al. ............ 585/21 |
| 4,922,047 A | * | 5/1990 | Chen et al. ............ 585/12 |
| 4,975,215 A | * | 12/1990 | Abe et al. ............ 252/73 |
| 5,126,065 A | * | 6/1992 | Tsubouchi et al. ...... 508/591 |
| 5,306,851 A | * | 4/1994 | Wu et al. ............ 585/22 |
| 5,344,582 A | * | 9/1994 | Umemoto et al. ...... 508/110 |
| 6,187,979 B1 | | 2/2001 | Ido et al. ............ 585/10 |
| 6,372,696 B1 | * | 4/2002 | Tipton ............ 508/110 |
| 6,395,689 B1 | | 5/2002 | Wagner et al. ............ 508/580 |

FOREIGN PATENT DOCUMENTS

| | | |
|---|---|---|
| EP | 0266848 A2 | 5/1988 |
| EP | 0402881 B1 | 12/1990 |
| EP | 0508292 B1 | 10/1992 |
| EP | 0526218 B1 | 2/1993 |

OTHER PUBLICATIONS

Molecular Design of Traction Fluids; A Novel Family of Traction Fluids Deriving from Molecular Design; Dare–Edwards, p. 197–205.

* cited by examiner

Primary Examiner—Ellen M. McAvoy
(74) Attorney, Agent, or Firm—Kathryn A. Marra (57) ABSTRACT

The present invention includes a traction fluid that includes an alkyl bridged dimer of bicycloheptane. Methods of using alkyl bridged dimers of bicycloheptane in traction fluids are also disclosed.

16 Claims, 3 Drawing Sheets

TRACTION FLUID WITH ALKANE BRIDGED DIMER

FIELD OF THE INVENTION

This invention relates to compounds, compositions and methods of using the compounds and compositions as traction fluids in toroidal continuously variable transmission (T-CVT) systems.

BACKGROUND OF THE INVENTION

A T-CVT system includes an input disk connected to the engine, an output disk connected to the wheels, and a pair of power rollers which engage the two disks and transfer drive power from the input disk to the output disk. A lubricant, called a traction fluid, lubricates the system and prevents the rollers from contacting the disks. Because the disks and roller never physically touch, the traction fluid also transfers drive power from the input disk to the rollers and then to the output disk. This contradiction of purposes leads to the adversarial nature of the physical properties needed by a traction fluid.

One constraint is the ability of any particular traction fluid to transfer power among the components of the T-CVT system. This ability is represented by the traction coefficient ($\mu_T$). The drive power is directly proportional to the $\mu_T$, thus a higher $\mu_T$ is advantageous.

Another constraint on the physical properties of a traction fluid is the range of temperatures at which a T-CVT must be operational. Start-up operating temperatures of T-CVT's may be as low as −40° C., while operating temperature could be as high as 140° C. Normal operating conditions will be in the range of 90° to 110° C. At the low end of the temperature range, the traction fluid must have a viscosity which is low enough to allow the traction fluid to flow and be pumped. At the high end of the range, the viscosity must be high enough to provide adequate lubrication. A flash point above 150° C. is desirable. In between the extremes of temperature, it is desirable to have the $\mu_T$ of the traction fluid independent of temperature. Furthermore, the viscosity of the traction fluid at the normal operating temperature is such that the fluid is retained on the rollers and disks of the T-CVT.

Traction fluids that are non-toxic to humans and posses a non-offensive odor, while also being inexpensive to manufacture are desirable.

While the large and heavy nature of T-CVT systems can be problematic, they do offer advantages that make them desirable, especially in terms of providing greater fuel economy in vehicles and machines. Generally, T-CVT systems provide at least 10% fuel efficiency over traditional automatic transmissions because the engine runs at its most efficient point independent of the vehicle speed. Since the traction fluid is responsible for the transfer of power to the wheels, the efficiency of a T-CVT system is related to $\mu_T$ and viscosity of the utilized traction fluid. Further, an increase in efficiency also allows for the reduction in size and weight of the T-CVT system.

Known traction fluids do not have acceptable physical properties. Particularly, some known traction fluids have a high $\mu_T$ at normal operating temperatures, but unacceptably high viscosities at low temperatures. Other known traction fluids have good low temperature viscosities, but the $\mu_T$ is unsatisfactory. Still other traction fluids have $\mu_T$ which are unacceptably dependent on temperature. Most known traction fluids suffer from difficult, expensive, and inefficient synthetic methods.

Exemplary known traction fluids include those based on 2,4-dicyclohexyl-2-methylpentane (DCMP) [CAS# 38970-72-8], which has a structure of:

Another known traction fluid is made from santene and isosantene (called FLUID X). The structure of the main component of this traction fluid is as follows:

Accordingly, the inventors have recognized a new class of traction fluids which overcome one or more of these problems which allow more efficient T-CVT systems.

SUMMARY OF THE INVENTION

The present invention includes a traction fluid that includes an alkyl bridged dimer of bicycloheptane. Methods of using alkyl bridged dimers of bicycloheptane in traction fluids are also disclosed.

BRIEF DESCRIPTION OF THE FIGURES

FIG. 1 compares the temperature dependence of the $\mu_T$ of the inventive traction fluids to that of the commercial fluids at a contact pressure of 1.27 GPa and slide-to-roll ratios of (a) 4% and (b) 1%.

FIG. 2 compares the pressure dependence of the $\mu_T$ of the inventive traction fluids to that of the commercial fluids at a temperature of 120° C. and slide-to-roll ratios of (a) 4% and (b) 1%.

DETAILED DESCRIPTION

The present invention is a traction fluid composition including a bicycloheptane dimer. Bicycloheptane dimers are two bicycloheptane moieties connected by an alkyl bridge. Bicycloheptane dimers useful in the present invention are described by the general formula X—Y—Z, where X and Z are the same or different bicycloheptane moieties and Y is a straight or branched alkyl bridge. The bicycloheptane moieties may be bicyclo[2.2.1]heptanyl, bicyclo[3.1.1]heptanyl, or bicyclo[4.1.0]heptanyl.

More particularly, these compounds may have at least one bicyclo[3.1.1]heptanyl moiety or bicyclo[2.2.1]heptanyl moiety. The following generic structures describe some useful classes of compounds in the present invention:

Formula I

Formula II

Formula III

Formula IV wherein $R_1$ and $R_3$ are, independently, H or straight or branched alkyl groups with 1 to 8 carbons, $R_2$ is straight or branched alkyl groups with 1 to 10 carbons, and x, y, z are, independently, 0 to 4.

Formula I includes compounds that contain two bicyclo[3.1.1]heptanyl moieties, while Formula II includes compounds with a bicyclo[3.1.1]heptanyl moiety and a bicyclo[2.2.1]heptanyl moiety. Formula III includes compounds which include a bicyclo[3.1.1]heptanyl moiety and a bicyclo[4.1.0]heptanyl moiety, while Formula IV includes compounds with a bicyclo[2.2.1]heptanyl moiety and a bicyclo[4.1.0]heptanyl moiety.

Useful subsets of bicycloheptane dimers include those which fall within the following generic structures:

Formula V

Formula VI

Formula VII

Formula VIII where g and h are, independently, 0 to 4 and $R_5$ and $R_6$ are independently, H or straight or branched alkyl groups with 1 to 8 carbons. The compounds of Formula V–VIII are methylene bridged dimers of bicycloheptane.

Most preferred compounds of the present invention are as follows:

Compound I

Compound II

Compound III

Compound IV

Compound V

Compound VI

Compound VII

Compound VIII

Compound IX

The compounds of Formulas I–VIII may be synthesized by the hydrogenation of appropriate olefin compounds. Useful olefin compounds are terpenes that are naturally occurring compounds and have the basic bicycloheptane or bicycloheptene ring structure already intact. Useful terpenes include α-pinene, β-pinene, norbornene, camphene and 3-carene. Other starting materials may be utilized, however, terpenes are preferred. The use of terpenes as starting materials is a significant advantage over known synthetic methods for traction fluids. Terpenes are naturally occurring fragrant compounds which are inexpensive to isolate and available in significant quantities. While other synthetic methods may be utilized, hydrogenation is preferred because the mechanism of hydrogenation is well understood. Together, the use of terpenes and hydrogenation lead to traction fluids that can be produced inexpensively and at high yields.

An acid catalyst is preferred to facilitate the hydrogenation reaction. Examples of the acid catalyst include a solid acid, such as activated clay, zeolite, montmorillonite; a Lewis acid, such as aluminum chloride, stannic chloride, boron trifluoride, boron trifluoride complex, boron tribromide, aluminum bromide; and an organic aluminum compound, such as triethylaluminum. An suitable Lewis acid catalyst includes boron trifluoride diethyl etherate $((C_2H_5)_2O\cdot BF_3)$.

Hydrogenation is usually performed in the presence of a metal catalyst in a pressurized $H_2$ atmosphere. Suitable catalysts include nickel, rhodium, ruthenium, palladium, platinum, and the like. Preferred catalysts include 0.1% to 20% wt % of nickel on diatomite, silica alumina or other substrate.

While a solvent is not required, a solvent may be used to facilitate the handling the starting materials and/or the catalysts, and for adjusting the progress of the reaction. Examples of appropriate solvents include saturated hydrocarbons (pentanes, hexanes, octanes, nonanes, and decanes), alicyclic hydrocarbons (cyclopentane, cyclohexane, methylcyclohexane and decalin), ether compounds (diethyl ether, THF, and butyl carbitol), halogen-containing compounds (chloroform, $MeCl_2$ and dichloroethane); and nitro-containing compounds (nitromethane and nitrobenzene).

Suitable $H_2$ pressures for hydrogenation include 50 to 3000 psi for 0.5 to 10 hours. The temperature range for the hydrogenation reaction is typically $-100°$ C. to $400°$ C.

Compounds I and II are synthesized by the hydrogenation reaction of β-pinene and α-pinene as shown in Reaction 1.

Compound III is synthesized by the hydrogenation reaction of β-pinene and norbornene as shown in Reaction 2.

These reaction conditions and starting materials may also result in other dimers, as shown in Reaction 2a and 2b.

Compounds IV and V are synthesized by the hydrogenation reaction of camphene and α-pinene as shown in Reaction 3.

Reaction 3

These reaction conditions and starting materials may also result in other dimers, as shown in Reaction 3a.

Reaction 3a

Compounds VI and VII are synthesized by the hydrogenation reaction of camphene and 3-carene, as shown in Reaction 4.

Reaction 4

Compound VII

These reaction conditions and starting materials may also result in other dimers, as shown in Reaction 4a.

Reaction 4a

Compounds VIII and IX are synthesized by the hydrogenation reaction β-pinene and 3-carene, as shown in Reaction 5.

Reaction 5

These reaction conditions and starting materials may also result in other dimers, as shown in Reaction 5a.

Reaction 5a

The preferred reaction conditions for the synthesis of Compounds I–IX are the use of 3 wt % Ni on diatomite at 160° C. 0.1 to 20% wt % of for four hours. After four hours, the reactor is slowly cooled to ambient temperature while maintaining the hydrogen pressure.

In addition, traction fluid compositions of the present invention may include pour point depressants, viscosity index improvers, anti-oxidants, corrosion inhibitors, extreme pressure agents, anti-wear agents and anti-foam agents.

EXAMPLES

Compound Preparation

Synthesis of 6,6-dimethyl-2-[[2,6,6-trimethylbicyclo[3.1.1] hept-3-yl]methyl]-bicyclo[3.1.1]heptane (Compound I) and 6,6-dimethyl-2-[[2,6,6-trimethylbicyclo[3.1.1]hept-2-yl] methyl]-bicyclo[3.1.1]heptane (Compound II) using α-Pinene and β-Pinene A 1 L 3-neck round bottom flask was fitted with an air-driven mechanical stirrer (with a Teflon blade), a septum, and a 2-neck adapter which was connected to a thermometer and a condenser (connected to a Firestone valve for the introduction of vacuum and argon), and was placed over an ice bath on a lab jack in case cooling was necessary. The flask was charged with 250.0 g of β-pinene [CAS #18172-67-3] and 250.0 g of α-pinene [CAS #80-56-8]. The system was placed under an inert argon atmosphere by cycling between vacuum and argon 6 times while stirring.

Using an oven-dried syringe, 8.3 mL (9.30 g, 1.9 wt % vs. the total olefins) of boron trifluoride diethyl etherate $((C_2H_5)_2 O \cdot BF_3)$ was introduced to the stirred mixture drop-wise through the septum over 35 minutes. External cooling with an ice bath was applied after the addition was completed.

The reaction was allowed to continue for a total of 4 h 4 min., at which time the reaction mixture was worked up as follows. 270 mL of 1M aqueous sodium hydroxide was added over 5 min. with vigorous stirring. To the resulting thick yellow emulsion, 500 mL of hexane was added. The organic layer was separated and washed with 270 mL of saturated aqueous NaCl solution. The inorganic layer was dried over 70 g of $MgSO_4$ and suction filtered. The $MgSO_4$ on the funnel was rinsed with 100 mL of hexane. The hexane was removed under vacuum (~10 mm Hg) on a rotary evaporator (38° C. bath) to give 482 g of liquid residue.

Part of the resulting residue (470 g) was combined with 14.3 g (3 wt %) of nickel on kieselguhr (diatomite) in a 600 mL Parr reactor. The reactor was purged with nitrogen by pressurizing to 250 psi and venting (twice), and then heated to 160° C. Hydrogen gas was introduced and the mixture was stirred at 600 psi/160° C. for 25 h, then at 600 psi/200° C. for an additional 13.25 h. After cooling to room temperature and venting, the catalyst was removed by suction filtration through a bed of Celite 545 to give 385 g of a clear, colorless liquid with a viscosity similar to motor oil. This residue was distilled in a Kugelrohr apparatus.

A 68.5 g fraction was collected up to 95° C./0.25 mm Hg. This was mainly unreacted starting materials by GC-FID analysis. A 279 g fraction was collected between 95° C. and 160° C. at 0.25 mm Hg. This material contained a colorless gel that separated from a fluid portion. The fluid portion was decanted away from the gel to give 255 g (FLUID 1). The remaining 4.2 g of gel was labeled FLUID 1-GEL.

Synthesis of 6,6-dimethyl-2-[[bicyclo[2.2.1]hept-2-yl] methyl]-bicyclo[3.1.1]heptane (Compound III) using β-Pinene and Norbornene A 2 L 3-neck round bottom flask was fitted with an air-driven mechanical stirrer (with a Teflon blade), a non-pressure-equalizing addition funnel (topped with a septum with a positive pressure of argon applied through a needle inlet), and a 2-neck adapter which was connected to a thermometer and a condenser (connected to a Firestone valve for the introduction of vacuum and argon), and was placed over an ice bath on a lab jack in case cooling was necessary. The flask was charged with and 250.3 g of norbornene [CAS #498-66-8] (the norbornene, mp 44–46° C., was melted on a steam bath to facilitate its transfer) and then with 250.3 g of β-pinene [CAS #18172-67-3]. The system was placed under an inert argon atmosphere by cycling between vacuum and argon 6 times while stirring.

Using an oven-dried syringe 8.9 mL (10.0 g, 2.0 wt % vs. the total olefins) of $(C_2H_5)_2O \cdot BF_3$ was introduced into the addition funnel through the septum and then added to the stirred mixture drop-wise over a 30 min. period. With this addition rate the reaction temperature rose to 39° C. during the addition without any external cooling of the flask. After an additional 2 h the temperature cooled to 23° C. as stirring at ambient temperature was continued. Three hours after completing the addition the temperature began to rise again and at 6.25 h it had reached 60° C. The ice bath was raised and lowered as needed over the next 20 min. to keep the temperature near 60° C. After that point the ice bath was not needed and the temperature gradually came down to 35° C. over the next hour.

The flask was placed in a 22° C. water bath and after stirring overnight (~16 h), the reaction mixture was worked up as follows. 270 mL of 1M aqueous sodium hydroxide was added with vigorous stirring. 750 mL of hexane was added to the resulting thick yellow emulsion. The organic layer was separated and washed with 270 mL of saturated aqueous NaCl solution. The inorganic layer was dried over 70 g of $MgSO_4$ and suction filtered with the $MgSO_4$ on the funnel rinsed with 100 mL of hexane. The hexane was removed under vacuum (~10 mm Hg) on a rotary evaporator (40° C. bath) to give 501.7 g of a thick, light yellow residue with a viscosity similar to warm tar.

Part of the resulting residue (485 g) was transferred into a 1L glass autoclave liner by first heating on a steam bath to allow the fluid to be poured. The liner was flushed with argon. 14.5 g (3 wt %) of nickel on kieselguhr, was added, and the liner was placed in a 3 liter rocking autoclave. The reactor was purged with nitrogen by pressurizing to 250 psi and venting (twice), and then heated to 158° C. Hydrogen gas was introduced and the mixture was rocked at 585 psi/158° C. for 16 h. After cooling to room temperature and venting, the residue was taken up in 500 mL of hexane, and the catalyst was removed by suction filtration through a bed (~2 inch thick) of Celite 545. After solvent removal (up to 90° C./10 mm Hg) on a rotary evaporator, a very thick, clear, colorless residue was obtained. This residue was distilled in a Kugelrohr apparatus.

A 138 g clear, colorless, slightly viscous fraction was collected between 98° C./0.50 mm Hg and 110° C./0.20 mm Hg (FLUID 2). Another more viscous distillation fraction was collected between 110–140° C./0.20 mm Hg to give 48 g (FLUID 2-GEL). The colorless residue in the pot turned into a glass at room temperature and weighed 228 g (FLUID 2-GLASS).

Synthesis of 2,2-dimethyl-3-[[2,6,6-trimethylbicyclo[3.1.1.] hept-3-yl]methyl]-bicyclo[2.2.1]heptane (Compound IV) and 2,2-dimethyl-3-[[2,6,6-trimethylbicyclo[3.1.1]hept-2-yl]methyl]-bicyclo[2.2.1]heptane (Compound V) using Camphene and α-Pinene A 2 L 3-neck round bottom flask was fitted with an air-driven mechanical stirrer (with a Teflon blade), a non-pressure-equalizing addition funnel (topped with a septum with a positive pressure of argon applied through a needle inlet), and a 2-neck adapter which: was connected to a thermometer and a condenser (connected to a Firestone valve for the introduction of vacuum and argon), and was placed over an ice bath on a lab jack in case cooling was necessary. The flask was charged with 250.9 g of camphene [CAS #79-92-5] (the camphene, mp 48–52° C., was melted on a steam bath to facilitate its transfer) and then with 251.1 g of α-pinene [CAS #80-56-8]. The system was placed under an inert argon atmosphere by cycling between vacuum and argon 6 times while stirring.

Using an oven-dried syringe 4.5 mL (5.04 g, 1.0 wt % vs. the total olefins) of $(C_2H_5)_2O.BF_3$ was introduced into the addition funnel through the septum and then added to the stirred mixture drop-wise over a 30 min. period. This addition rate kept the reaction temperature near 30° C. without any external cooling of the flask.

After an additional 30 min. the temperature was down to 23° C. and the mixture was stirred at room temperature for 3.5 more hours before recharging the addition funnel with another 4.5 mL (5.04 g, 1.0 wt % vs. the total olefins) of $(C_2H_5)_2O.BF_3$. Drop-wise addition of this portion of $(C_2H_5)_2 O.BF_3$ over 23 min. global kept the temperature below 30° C., but in the 6 min. period after completing the addition, the temperature rose to 55° C. The ice bath was raised and lowered as needed over the next 20 min. to keep the temperature near 55° C. After that point the ice bath was not needed and the temperature gradually came down to room temperature over the next 75 min.

After stirring overnight (~16 h) the reaction mixture was worked up as follows. 270 mL of 1M aqueous sodium hydroxide was added with vigorous stirring. 500 mL of hexane was added to the resulting thick yellow emulsion. The organic layer was separated and washed with 270 mL of saturated aqueous NaCl solution. The hexane layer was dried over 70 g of $MgSO_4$ and suction filtered. The $MgSO_4$ on the funnel was rinsed with 100 mL of hexane. The hexane was removed under vacuum (~10 mm Hg) on a rotary evaporator (38° C. bath) to give 501 g of liquid residue.

Part of the resulting residue (476 g) was combined with 14.4 g (3 wt %) of nickel on kieselguhr in a 600 mL Parr reactor. The reactor was purged with nitrogen by pressurizing to 250 psi and venting (twice), and then heated to 160° C. Hydrogen gas was introduced and the mixture was stirred at 570 psi/200° C. for 19 h. After cooling to room temperature and venting, the catalyst was removed by suction filtration through a bed (~2 inch thick) of Celite 545 to give a clear colorless liquid with a viscosity similar to motor oil. This residue was distilled in a Kugelrohr apparatus.

A 170 g fraction was collected up to 100° C./0.20 mm Hg. This was mainly unreacted starting materials by GC-FID analysis. The main fraction was collected between 110° C./0.30 mm Hg and 155° C./0.20 mm Hg. This material contained a colorless gel that separated from the fluid portion. The fluid portion was decanted away from the gel to give 244 g (FLUID 3). The remaining 18.1 g of gel was labeled FLUID 3-GEL.

Synthesis of 2,2-dimethyl-3-[[3,7,7-trimethylbicyclo[4.1.0] hept-4-yl]methyl]-bicyclo[2.2.1]heptane (Compound VI) and 2,2-dimethyl-3-[[3,7,7-trimethylbicyclo[4.1.0]hept-3-yl]methyl]-bicyclo[2.2.1]heptane (Compound VII) using Camphene and 3-Carene A 2 L 3-neck round bottom flask was fitted with an air-driven mechanical stirrer (with a Teflon blade), a non-pressure-equalizing addition funnel (topped with a septum with a positive pressure of argon applied through a needle inlet), and a 2-neck adapter which was connected to a thermometer and a condenser (connected to a Firestone valve for the introduction of vacuum and argon), and was placed over an ice bath on a lab jack in case cooling was necessary. The flask was charged with and 250.0 g of camphene [CAS #79-92-5] (the camphene, mp 48–52° C., was melted on a steam bath to facilitate its transfer) and then with 250 g of 3-carene [CAS #13466-78-9]. The system was placed under an inert argon atmosphere by cycling between vacuum and argon 6 times while stirring.

Using an oven-dried syringe 8.9 mL (10.0 g, 2.0 wt % vs. the total olefins) of $(C_2H_5)_2O.BF_3$ was introduced into the addition funnel through the septum and then added to the stirred mixture drop-wise over a 45 min. period. This addition rate kept the reaction temperature near 30° C. without any external cooling of the flask, but in the 6 min. period after completing the addition the temperature rose to 60° C. The ice bath was raised and lowered as needed over the next 30 min. to keep the temperature near 60° C. After that point the ice bath was not needed and the temperature gradually came down to room temperature over the next 60 min.

After stirring overnight (~19 h) the reaction mixture was worked up as follows. 270 mL of 1M aqueous sodium hydroxide was added with vigorous stirring. 500 mL of hexane was added to the resulting thick yellow emulsion; the organic layer was separated and washed with 270 mL of saturated aqueous NaCl solution. The hexane layer was dried over 70 g of $MgSO_4$ and suction filtered. The $MgSO_4$ on the funnel was rinsed with 100 mL of hexane. The hexane was removed under vacuum (~10 mm Hg) on a rotary evaporator (40° C. bath) to give 490 g of liquid residue.

Part of the resulting residue (480 g) was transferred into a 1L glass autoclave liner, and the liner was flushed with argon. Nickel (60% on kieselguhr), 14.4 g (3 wt %), was added, and the liner was placed in a 3 liter rocking autoclave. The reactor was purged with nitrogen by pressurizing to 250 psi and venting (twice), pressurized with hydrogen gas, and then heated. The mixture was rocked at 580 psi/159° C. for 16 h. After cooling to room temperature and venting, the catalyst was removed by suction filtration of the neat residue through a bed (~2 inch thick) of Celite 545. The resulting liquid was vacuum distilled using a simple distillation head.

A 203 g clear, colorless, slightly viscous fraction was collected between 109–111° C./0.05 mm Hg (FLUID 4). Another 72 g clear, colorless, slightly viscous fraction was collected between 111–145° C./0.05 mm Hg (about half of it between 126–130° C.) (FLUID 4-GEL). The pot residue was a cloudy, colorless, non-flowing residue that weighed 38 g (FLUID 4-GLASS).

Synthesis of 6,6-dimethyl-2-[[3,7,7-trimethylbicyclo[4.1.0]hept-4-yl]methyl]-bicyclo[3.1.1]heptane (Compound VIII) and 6,6-dimethyl-2-[[3,7,7-trimethylbicyclo[4.1.0]hept-3-yl]methyl]-bicyclo[3.1.1]heptane (Compound IX) using β-Pinene and 3-Carene A 2 L 3-neck round bottom flask was fitted with an air-driven mechanical stirrer (with a Teflon blade), a non-pressure-equalizing addition funnel (topped with a septum with a positive pressure of argon applied through a needle inlet), and a 2-neck adapter which was connected to a thermometer and a condenser (connected to a Firestone valve for the introduction of vacuum and argon), and was placed over an ice bath on a lab jack in case cooling was necessary. The flask was charged with and 291 mL (250 g) of β-pinene [CAS #18172-67-3] and then with 291.7 (250 g) of 3-carene [CAS #13466-78-9]. The system was placed under an inert argon atmosphere by cycling between vacuum and argon 6 times while stirring.

Using an oven-dried syringe 8.9 mL (10.0 g, 2.0 wt % vs. the total olefins) of $(C_2H_5)_2O.BF_3$ was introduced into the addition funnel through the septum and then added to the stirred mixture drop-wise over a 60 min. period. The reaction temperature rose and the solution became orange-red in color. After the first 5.2 mL of $(C_2H_5)_2O.BF_3$ had been added (25 min.) intermittent ice cooling was applied to maintain the reaction temperature near 60° C. as the addition was continued. Ten minutes after the addition was complete the ice bath was not needed and the temperature gradually returned to room temperature over the next 2 h.

After stirring overnight (~20 h) the reaction mixture was worked up as follows: 270 mL of 1M aqueous sodium hydroxide was added with vigorous stirring. 500 mL of hexane was added to the resulting thick yellow emulsion; the organic layer was separated and washed with 270 mL of saturated aqueous NaCl solution. The hexane layer was stored over the weekend at room temperature, then dried over 70 g of $MgSO_4$, and suction filtered. The $MgSO_4$ on the funnel was rinsed with 100 mL of hexane. The hexane was removed under vacuum (~10 mm Hg) on a rotary evaporator (40° C. bath) to give 487 g of viscous liquid residue.

Part of the resulting residue (485 g) was transferred into a 1L glass autoclave liner, and the liner was flushed with nitrogen. 14.5 g (3 wt %) of nickel on kieselguhr was added, and the liner was placed in a 3 liter rocking autoclave. The reactor was purged with nitrogen by pressurizing to 250 psi and venting (twice), then pressurized with 500 psi of hydrogen gas, and heated to 161° C. The mixture was rocked at 580 psi/161° C. for 16 h. After venting, the catalyst was removed by suction filtration of the hot (~80–100° C.) neat residue through a bed (~2 inch thick) of Celite 545 (the Buchner funnel was warmed with a heat gun to keep the residue flowing). The resulting viscous, colorless liquid weighed 359 g and was vacuum distilled using a simple distillation head initially. Distillation was then switched to a kugelrohr apparatus to distill material from the very thick residue obtained after the lower boiling fractions were removed.

A 110 g clear, colorless, slightly viscous fraction was collected between 111–123° C./0.05 mm Hg (FLUID 5) using the simple distillation set up. Another 58 g clear, colorless, very viscous fraction was collected between 135–170° C./0.05 mm Hg on the kugelrohr apparatus (FLUID 5-GEL). The pot residue was a cloudy, colorless, glass that weighed 141 g (FLUID 5-GLASS).

Characterization of FLUID 1–5

Each of FLUID 1–5 was redistilled using a rotary evaporator in preparation for characterization. The redistilled fluids were dissolved in $MeCl_2$ to a nominal concentration of 100 ppm (0.01 wt %). Reference materials, distilled FLUID X and DCMP fluids were also dissolved in a similar manner. This solvent dissolved all the fluids and made it possible to obtain relative semi-quantitative information on all eluting components.

Data was collected using a Hewlett Packard (HP) Model 5973 mass selective detector (MS) connected to a HP Model 6890+ Series gas chromatograph (GC). Sample introduction was made with a HP microliter syringe by auto-injecting a 0.2 μL aliquot of the $MeCl_2$ extract samples via HP 7863 Series automated injector. A 30 m length×0.250 mm I.D.× 0.25 μm (5%-Phenyl)-methylpolysiloxane film thickness HP-5 MS capillary column was used. The system was controlled by an HP Enhanced ChemStation. The MS was calibrated using perfluorotributylamine calibration standard from Agilent Technologies.

All the tested fluids, FLUID 1–5 along with distilled FLUID X and DCMP commercially available fluids, were analyzed using the above described GC-MS system to determine the purity of each primary and secondary constituent. FLUID 1 contained 84% Compound I and Compound II. FLUID 1 also contained 16% secondary constituent dimers. FLUID 2 contained 12% Compound III and 88% trimers and secondary constituents dimers. Additional physical testing was not performed on FLUID 2. FLUID 3 contained 78% Compound IV and Compound V, while also containing 22% secondary constituent dimers. FLUID 4 contained 73% Compounds VI and Compound VII and 27% secondary constituent dimers. FLUID 5 contained 80% Compound VIII and Compound IX, with 20% secondary constituent dimer. Secondary constituent dimers include compounds of Formulas I–IV, where y is 0 and are shown in Reactions 1a, 2a, 3a, 4a and 5a. GC-MS data for FLUID X and DCMP confirmed structure and purity of these fluids.

Traction Coefficients

The traction coefficient, $\mu_T$, of each of FLUID 1 and 3–5 ("the tested FLUIDS") and the commercial traction fluids, FLUID X and DCMP, were obtained with a PCS Instruments Model M110 ball-on-disc mini-traction apparatus. Traction tests on the fluids were made using ¾-in 52100 steel balls at a maximum Hertzian contact pressure (P) of 0.992, 1.15, and 1.27 GPa with a fluid entrainment velocity of ~2.8 m/s. At each contact pressure, $\mu_T$ was measured at temperatures ranging between 40° C. and 150° C.

Figure 1A:
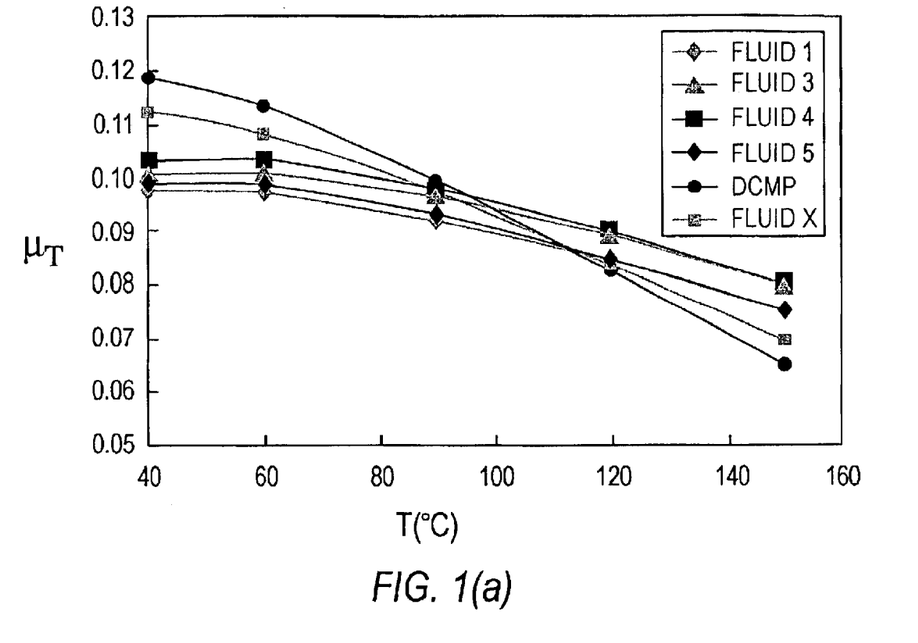
Figure 1B:
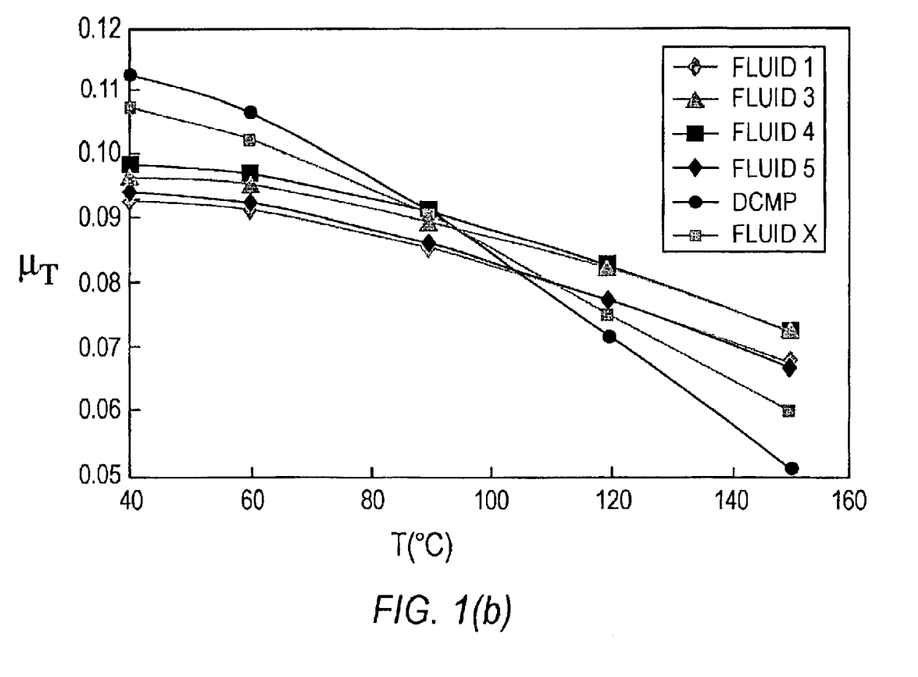

The temperature dependence of the traction coefficients was measured with a contact pressure of 1.27 GPa and slide-to-roll ratios (SRR) of 4% and 1%, with the results shown in FIGS. 1(a) and 1(b). These figures reveal that at 40° C. the commercial traction fluids have a higher $\mu_T$ than the tested FLUIDS. However, as the temperature increases, the $\mu_T$ for the tested FLUIDS exceed those of DCMP and FLUID X between 75° C. and 120° C. As can be seen from FIGS. 1(a) and 1(b), the tested FLUIDS are less temperature dependent than the commercially available fluids.

Figure 2A:
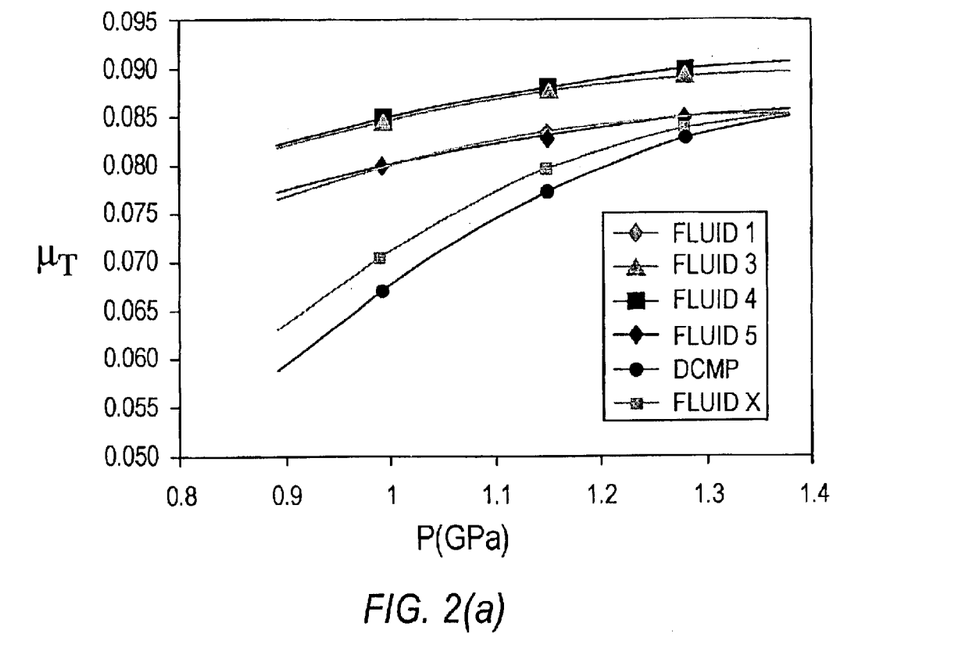
Figure 2B:
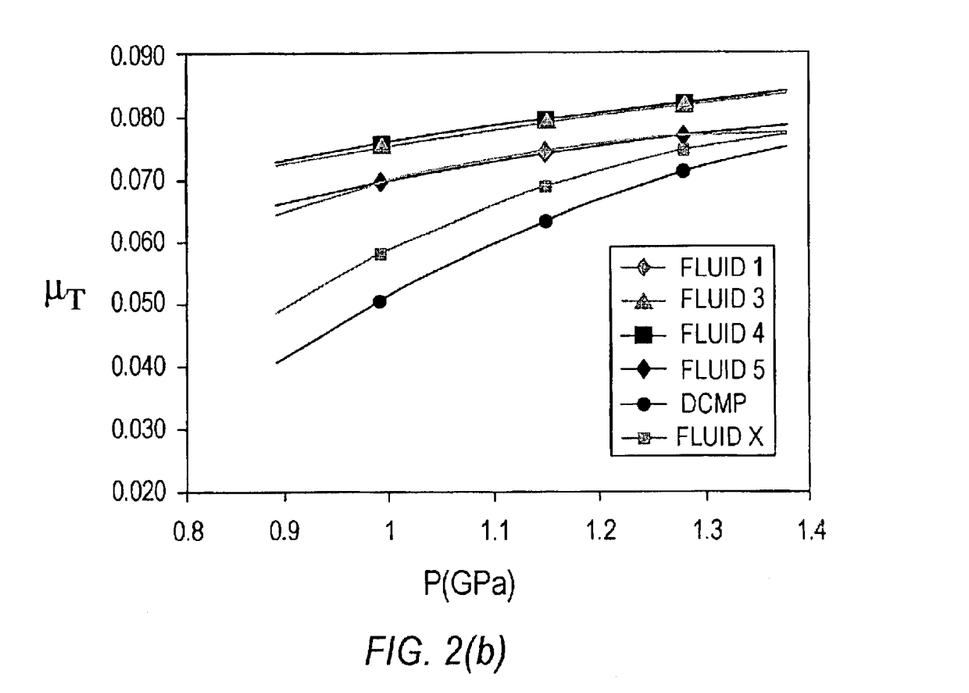

The pressure dependence of the traction coefficients were measured at a temperature of 120° C. and SRR of 4% and 1%, with the results shown in FIGS. 2(a) and 2(b). These figures reveal that at measured pressures, the tested FLUIDS all have higher $\mu_T$ than the commercially available fluids and are less pressure dependent than the commercially available fluids.

Figure 3:
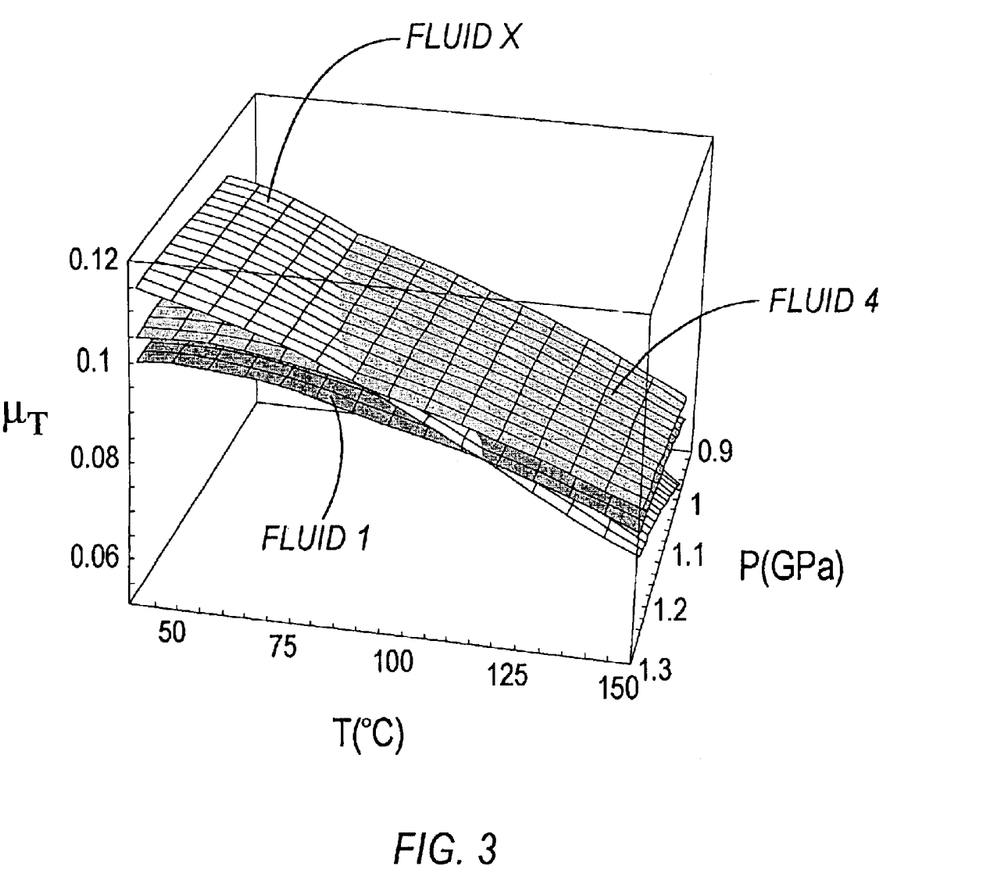
FIG. 3 compares the temperature and pressure dependences of the $\mu_T$ of the inventive FLUID 1 and FLUID 4 to that of the commercial traction fluid FLUID X.

FIG. 3 shows the temperature and pressure dependence of FLUID 1, FLUID 4 and FLUID X. The temperature and pressure dependence of FLUID 3 and FLUID 5 generally fall between that of FLUID 4 and FLUID 1. As can be seen from the FIG. 3, the $\mu_T$ of the tested FLUIDS are much less dependent on pressure and temperature than the traction coefficient of FLUID X, which exhibits a strong dependence on both temperature and pressure. The independence of the $\mu_T$ of the tested FLUIDS makes them suitable for use as traction fluids per se or in combination with other components.

While the invention has been specifically described in connection with certain specific embodiments thereof, it is to be understood that this is by way of illustration and not of limitation, and the scope of the appended claims should be construed as broadly as the prior art will permit.

What is claimed is:

1. A composition comprising a traction fluid that includes at least one compound according to at least one of the following formulas:

wherein $R_1$ and $R_3$ are, independently, H or straight or branched alkyl groups with 1 to 8 carbons, $R_2$ is straight or branched alkyl groups with 1 to 10 carbons, and x, y, z are, independently, 0 to 4.

2. The composition of claim 1, wherein the traction fluid includes at least one compound according to at least one of the following formulas:

wherein g and h are, independently, 0 to 4 and $R_5$ and $R_6$ are, independently, straight or branched alkyl groups with 1 to 8 carbons.

3. The composition of claim 1 wherein the traction fluid includes at least one compound selected from:

4. The composition of claim 2 wherein the traction fluid includes:

5. The composition of claim 2 wherein the traction fluid includes:

6. The composition of claim 2 wherein the traction fluid includes:

7. The composition of claim 2 wherein the traction fluid includes:

or

8. The composition of claim 2 wherein the traction fluid includes:

or

9. The composition of claim 2, wherein the traction fluid includes:
6,6-dimethyl-2-[[2,6,6-trimethylbicyclo[3,1,1]hept-3-yl]methyl]-bicyclo[3,1,1]heptane, 6,6-dimethyl-2-[[2,6,6-trimethylbicyclo[3,1,1]hept-2-yl]methyl]-bicyclo[3,1,1]heptane, 6,6-dimethyl-2-[[bicyclo[2,2,1]hept-2-yl]methyl]-bicyclo[3,1,1]heptane, 2,2-dimethyl-3-[[3,7,7-trimethylbicyclo[4,1,0]hept-4-yl]methyl]-bicyclo[2,2,1]heptane, 2,2-dimethyl-3-[[3,7,7-trimethylbicyclo[4,1,0]hept-3-yl]methyl]-bicyclo[2,2,1]heptane, 2,2-dimethyl-3-[[3,7,7-trimethylbicyclo[4,1,0]hept-4-yl]methyl]-bicyclo[2,2,1]heptane, 2,2-dimethyl-3-[[3,7,7-trimethylbicyclo[4,1,0]hept-3-yl]methyl]-bicyclo[2,2,1]heptane, 6,6-dimethyl-2-[[3,7,7-trimethylbicyclo[4,1,0]hept-4-yl]methyl]-bicyclo[3,1,1]heptane, 6,6-dimethyl-2-[[3,7,7-trimethylbicyclo[4,1,0]hept-3-yl]methyl]-bicyclo[3,1,1]heptane.

10. The composition of claim 1, wherein the traction fluid includes at least one compound where y is 0.

11. The composition of claim 10, wherein the traction fluid includes compounds where y is 0 and y is 1.

12. A method of operating a transmission, comprising:
lubricating a toroidal continuously variable transmission with a traction fluid that includes at least one compound according to at least one of the following formulas:

wherein $R_1$ and $R_3$ are, independently, H or straight or branched alkyl groups with 1 to 8 carbons, $R_2$ is straight or branched alkyl groups with 1 to 10 carbons, and x, y, z are, independently, 0 to 4.

13. The method of claim 10, wherein the traction fluid includes at least one compound according to at least one of the following formulas:

wherein g and h are 0 to 4 and $R_5$ and $R^6$ are, independently, alkyl groups with 1 to 8 carbons.

14. The method of claim 12, wherein the traction fluid includes at least one compound selected from:

-continued

, and

-continued

.

15. The method of claim 12, wherein the traction fluid includes at least one compound where y is 0.

16. The method of claim 14, wherein the traction fluid includes compounds wherein y=0 and y is 1.

* * * * *